(12) United States Patent  
Koshino (10) Patent No.: US 12,318,244 B2
(45) Date of Patent: Jun. 3, 2025

(54) ULTRASOUND DIAGNOSTIC APPARATUS AND CONTROL METHOD OF ULTRASOUND DIAGNOSTIC APPARATUS

(71) Applicant: FUJIFILM Corporation, Tokyo (JP)

(72) Inventor: Riko Koshino, Tokyo (JP)

(73) Assignee: FUJIFILM Corporation, Tokyo (JP)

(*) Notice: Subject to any disclaimer, the term of this patent is extended or adjusted under 35 U.S.C. 154(b) by 83 days.

(21) Appl. No.: 18/462,277

(22) Filed: Sep. 6, 2023

(65) Prior Publication Data

US 2023/0414194 A1     Dec. 28, 2023

Related U.S. Application Data

(63) Continuation of application No. PCT/JP2022/002018, filed on Jan. 20, 2022.

(30) Foreign Application Priority Data

Mar. 19, 2021 (JP) .................... 2021-045454

(51) Int. Cl.
*A61B 8/08* (2006.01)
*A61B 8/00* (2006.01)

(52) U.S. Cl.
CPC .............. *A61B 8/08* (2013.01); *A61B 8/461* (2013.01); *A61B 8/5238* (2013.01)

(58) Field of Classification Search
CPC ....... G06T 7/0012; A61B 8/08; A61B 8/0833; A61B 8/0825; A61B 8/52; A61B 8/5215; A61B 8/5223

See application file for complete search history.

(56) References Cited

U.S. PATENT DOCUMENTS 5,487,387 A      1/1996 Trahey et al.
2015/0173717 A1  6/2015 Tanigawa

FOREIGN PATENT DOCUMENTS

JP   2012-055742 A   3/2012
JP   2015-119819 A   7/2015
(Continued)

OTHER PUBLICATIONS

The extended European search report issued by the European Patent Office on Aug. 7, 2024, which corresponds to European Patent Application No. 22770850.0-1122 and is related to U.S. Appl. No. 18/462,277.

(Continued)

*Primary Examiner* — Carolyn A Pehlke
(74) *Attorney, Agent, or Firm* — Studebaker Brackett PLLC (57) ABSTRACT

An ultrasound diagnostic apparatus includes a debris specifying unit 25 that specifies debris in the cyst from each of a first ultrasound image acquired by the image acquisition unit 41, and a second ultrasound image acquired by the image acquisition unit 41 by imaging the cyst from the same direction as a direction in a case of capturing the first ultrasound image with respect to the cyst after an external force different from an external force in a case of capturing the first ultrasound image has acted on the cyst or in a state where the external force is acting on the cyst, and a debris movement information providing unit 26 that provides information regarding movement of the debris, which is specified by the debris specifying unit 25, in the cyst between the first ultrasound image and the second ultrasound image.

20 Claims, 8 Drawing Sheets

(56) References Cited

FOREIGN PATENT DOCUMENTS

JP       2019-118647 A    7/2019
WO       2020/240455 A1   12/2020

OTHER PUBLICATIONS

Athanasiou A. et al., "Complex cystic breast masses in ultrasound examination", Diagnostic and Interventional Imaging, vol. 95, No. 2, Feb. 1, 2014, pp. 169-179, doi: 10.1016/j.diii.2013.12.008.
International Search Report issued in PCT/JP2022/002018; mailed Apr. 19, 2022.
International Preliminary Report On Patentability (Chapter I) and Written Opinion of the International Searching Authority issued in PCT/JP2022/002018; issued Sep. 12, 2023.

ULTRASOUND DIAGNOSTIC APPARATUS AND CONTROL METHOD OF ULTRASOUND DIAGNOSTIC APPARATUS

CROSS-REFERENCE TO RELATED APPLICATIONS

This application is a Continuation of PCT International Application No. PCT/JP2022/002018 filed on Jan. 20, 2022, which claims priority under 35 U.S.C. § 119(a) to Japanese Patent Application No. 2021-045454 filed on Mar. 19, 2021. The above applications are hereby expressly incorporated by reference, in their entirety, into the present application.

BACKGROUND OF THE INVENTION

1. Field of the Invention

The present invention relates to an ultrasound diagnostic apparatus that diagnoses a cyst of a subject and a control method of the ultrasound diagnostic apparatus.

2. Description of the Related Art

In the related art, in a medical field, an ultrasound diagnostic apparatus using an ultrasound image has been put into practical use. In general, the ultrasound diagnostic apparatus comprises an ultrasound probe in which a transducer array is provided and an apparatus main body connected to the ultrasound probe. An ultrasound beam is transmitted from the ultrasound probe toward a subject, an ultrasound echo from the subject is received by the ultrasound probe, and a reception signal is electrically processed. Thereby, an ultrasound image is generated.

A cyst is known as a pathological condition in which secretions accumulate in a sac-like shape, but in a case in which the cyst is observed with the ultrasound diagnostic apparatus, debris, which is an echogenic composition that reflects ultrasound waves, is confirmed inside the cyst in many cases. In a case in which the debris has fluidity, it is found that the debris consists of mucous secretions, and in this case, the cyst is a so-called complicated cyst, which is usually benign and not a target of treatment. On the other hand, in a case in which the debris is solid, there is a suspicion of a so-called complex cyst, in which a tumor is present in the cyst.

Therefore, for example, JP2019-118647A discloses an ultrasound diagnostic apparatus that transmits an ultrasound beam twice to a cyst, detects a movement of the cyst, and discriminates a type of the cyst. The type of the cyst is discriminated based on a difference in temporal changes in parameters of the movement of the cyst in a case in which an acoustic radiation force of the ultrasound beam is applied to the cyst.

SUMMARY OF THE INVENTION

However, the ultrasound diagnostic apparatus in JP2019-118647A obtains the temporal change in parameters of the movement of the cyst due to the two times of transmission of the ultrasound beam, but it is not possible to clearly detect which part of the cyst has moved, which makes it difficult to easily recognize whether only debris in the cyst has moved or the entire cyst, including the debris, has moved.

The present invention has been made to solve such a problem in the related art, and an object of the present invention is to provide an ultrasound diagnostic apparatus capable of easily recognizing movement of debris in a cyst and a control method of the ultrasound diagnostic apparatus.

In order to achieve the above object, according to the present invention, there is provided an ultrasound diagnostic apparatus comprising: an image acquisition unit that acquires an ultrasound image obtained by imaging a cyst of a subject by transmitting and receiving an ultrasound wave to and from the subject; a monitor that displays the ultrasound image; a debris specifying unit that specifies debris in the cyst from each of a first ultrasound image acquired by the image acquisition unit, and a second ultrasound image acquired by the image acquisition unit by imaging the cyst from the same direction as a direction in a case of capturing the first ultrasound image with respect to the cyst after an external force different from an external force in a case of capturing the first ultrasound image has acted on the cyst or in a state where the external force is acting on the cyst; and a debris movement information providing unit that provides information regarding movement of the debris, which is specified by the debris specifying unit, in the cyst between the first ultrasound image and the second ultrasound image.

It is preferable that the debris specifying unit specifies the cyst from each of the first ultrasound image and the second ultrasound image, and specifies debris in the specified cyst.

In addition, it is preferable that the debris specifying unit specifies the debris in a state where the cyst specified from the first ultrasound image and the cyst specified from the second ultrasound image are registered with each other.

The debris specifying unit may be configured to include a confirmation unit that issues a message to a user to confirm that the cyst is imaged in the second ultrasound image from the same direction as the direction in a case of capturing the first ultrasound image.

Alternatively, the debris specifying unit may be configured to include an identity determination unit that determines whether or not the same cyst is imaged by image recognition of each of the first ultrasound image and the second ultrasound image.

The identity determination unit may detect an edge from each of the first ultrasound image and the second ultrasound image, obtain a movement vector in which the edge is moved between the first ultrasound image and the second ultrasound image, and determine that the same cyst is imaged in a case in which the movement vector falls within an allowable range.

Alternatively, the identity determination unit may determine whether or not the same cyst is imaged by a trained determination model in which the first ultrasound image and the second ultrasound image are used as an input.

It is preferable that the debris movement information providing unit displays, on the monitor, the cyst in the first ultrasound image and the cyst in the second ultrasound image registered with each other by the debris specifying unit.

The debris movement information providing unit may display the cyst in the first ultrasound image and the cyst in the second ultrasound image side by side on the monitor, or may display the cyst in the first ultrasound image and the cyst in the second ultrasound image in a superimposed manner on the monitor.

In addition, the debris movement information providing unit may be configured to include a debris movement determination unit that determines whether or not a movement amount of the debris in the cyst between the first ultrasound image and the second ultrasound image exceeds a threshold value by image recognition of each of the first ultrasound image and the second ultrasound image and that displays a determination result on the monitor.

According to the present invention, there is provided a control method of an ultrasound diagnostic apparatus, the method comprising: acquiring a first ultrasound image obtained by imaging a cyst of a subject; displaying the first ultrasound image on a monitor; acquiring a second ultrasound image obtained by imaging the cyst from the same direction as a direction in a case of capturing the first ultrasound image with respect to the cyst after an external force different from an external force in a case of capturing the first ultrasound image has acted on the cyst or in a state where the external force is acting on the cyst; specifying debris in the cyst from each of the first ultrasound image and the second ultrasound image; and providing information regarding movement of the debris in the cyst between the first ultrasound image and the second ultrasound image.

According to the present invention, the debris specifying unit specifies debris in the cyst from each of a first ultrasound image acquired by the image acquisition unit, and a second ultrasound image acquired by the image acquisition unit by imaging the cyst from the same direction as a direction in a case of capturing the first ultrasound image with respect to the cyst after an external force different from an external force in a case of capturing the first ultrasound image has acted on the cyst or in a state where the external force is acting on the cyst, and a debris movement information providing unit provides information regarding movement of the debris in the cyst between the first ultrasound image and the second ultrasound image, so that it is possible to easily recognize the movement of the debris in the cyst.

DESCRIPTION OF THE PREFERRED EMBODIMENTS

Hereinafter, embodiments of the present invention will be described with reference to the accompanying drawings.

Description of constituents described below may be made based on a typical embodiment of the present invention, but the present invention is not limited to such an embodiment.

In the present specification, the numerical range represented by "to" means a range including numerical values denoted before and after "to" as a lower limit value and an upper limit value.

In the present specification, the terms "same" and "identical" include an error range generally allowed in the technical field.

First Embodiment

Figure 1:
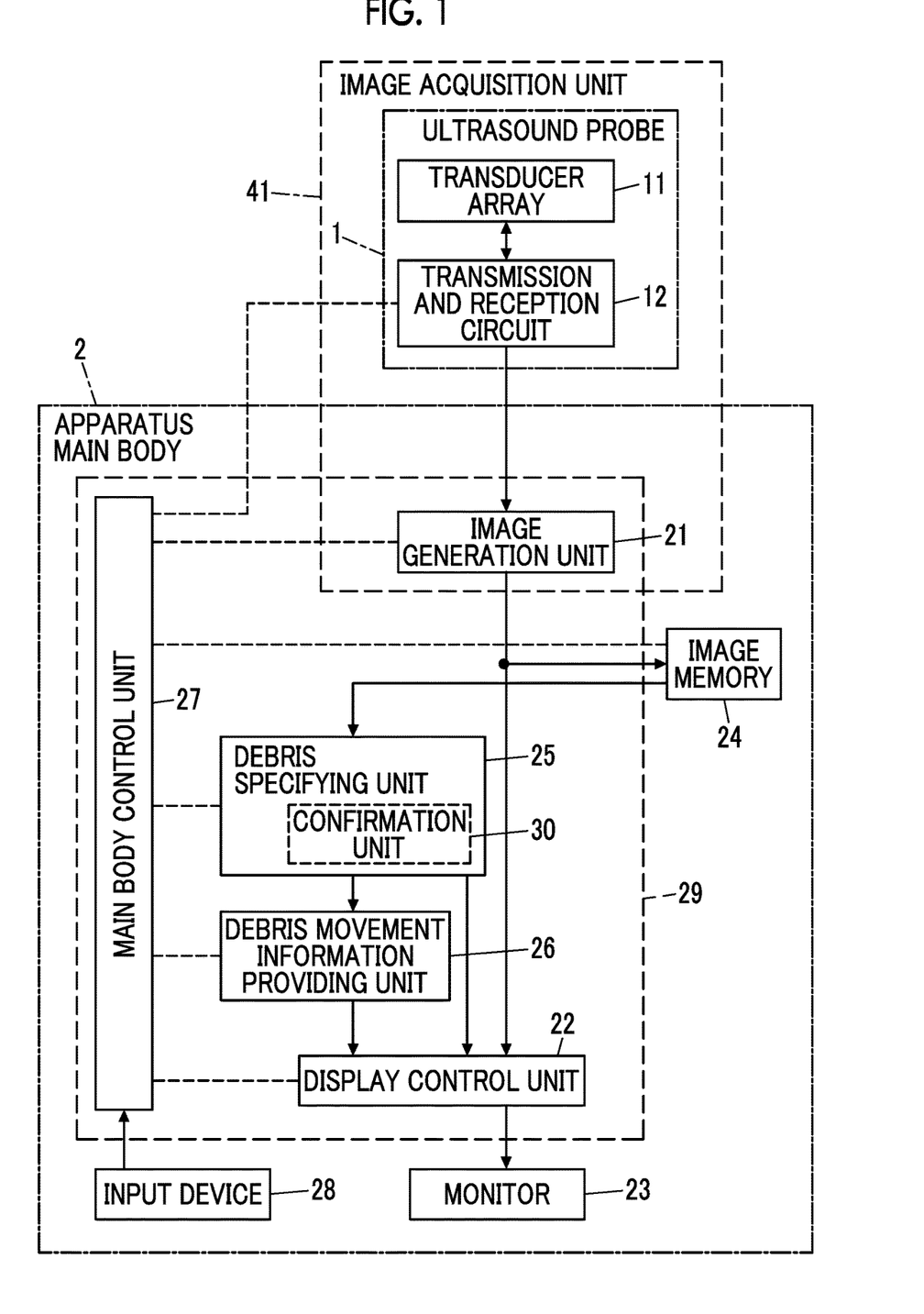
FIG. 1 is a block diagram showing a configuration of an ultrasound diagnostic apparatus according to a first embodiment of the present invention.

FIG. 1 shows a configuration of an ultrasound diagnostic apparatus according to a first embodiment of the present invention. The ultrasound diagnostic apparatus comprises an ultrasound probe 1 and an apparatus main body 2. The ultrasound probe 1 and the apparatus main body 2 are wired-connected to each other via a cable (not shown).

The ultrasound probe 1 includes a transducer array 11 and a transmission and reception circuit 12 connected to the transducer array 11.

The apparatus main body 2 includes an image generation unit 21 connected to the transmission and reception circuit 12 of the ultrasound probe 1. A display control unit 22 and a monitor 23 are sequentially connected to the image generation unit 21, and an image memory 24 is connected to the image generation unit 21. In addition, a debris specifying unit 25 and a debris movement information providing unit 26 are sequentially connected to the image memory 24, and the debris specifying unit 25 and the debris movement information providing unit 26 are connected to the display control unit 22.

A main body control unit 27 is connected to the image generation unit 21, the display control unit 22, the image memory 24, the debris specifying unit 25, and the debris movement information providing unit 26, and an input device 28 is connected to the main body control unit 27. In addition, the transmission and reception circuit 12 of the ultrasound probe 1 is connected to the main body control unit 27.

A processor 29 is configured of the image generation unit 21, the display control unit 22, the debris specifying unit 25, the debris movement information providing unit 26, and the main body control unit 27.

The debris specifying unit 25 has a confirmation unit 30 inside.

An image acquisition unit 41 is formed by the ultrasound probe 1 and the image generation unit 21 of the apparatus main body 2.

The transducer array 11 of the ultrasound probe 1 has a plurality of ultrasound transducers arrayed one-dimensionally or two-dimensionally. Each of these transducers transmits an ultrasound wave in response to a drive signal supplied from the transmission and reception circuit 12, receives a reflected wave from a subject, and outputs an analog reception signal. For example, each transducer is configured by forming electrodes at both ends of a piezoelectric body consisting of piezoelectric ceramic represented by lead zirconate titanate (PZT), a polymeric piezoelectric element represented by poly vinylidene di fluoride (PVDF), piezoelectric single crystal represented by lead magnesium niobate-lead titanate (PMN-PT), or the like.

Figure 2:
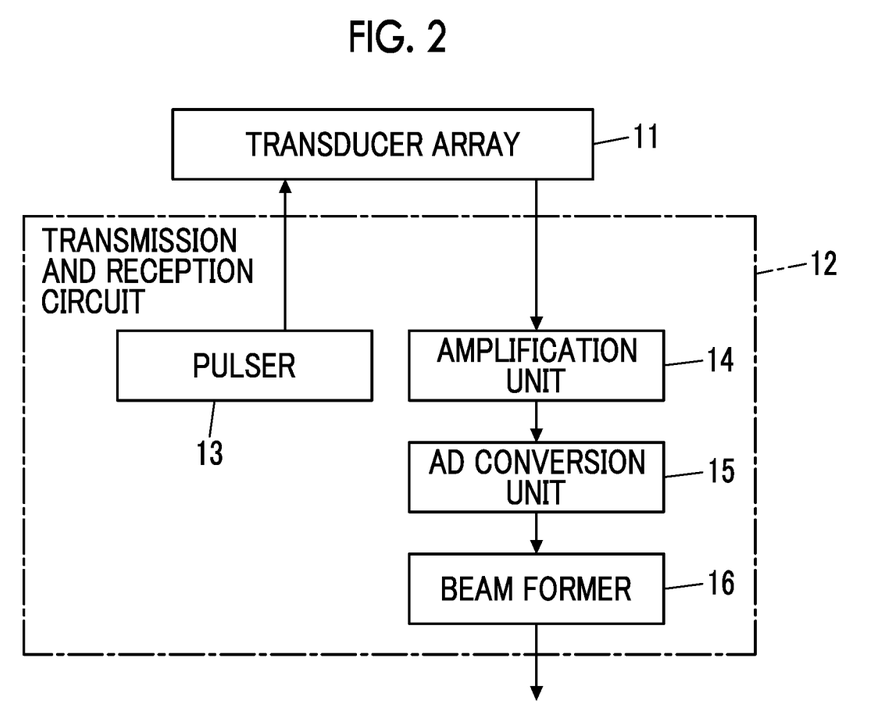
FIG. 2 is a block diagram showing an internal configuration of a transmission and reception circuit in the first embodiment.

The transmission and reception circuit 12 causes the transducer array 11 to transmit the ultrasound wave and generates a sound ray signal based on a reception signal acquired by the transducer array 11, under the control of the main body control unit 27. As shown in FIG. 2, the transmission and reception circuit 12 includes a pulser 13 connected to the transducer array 11, and an amplification unit 14, an analog-to-digital (AD) conversion unit 15, and a beam former 16 which are sequentially connected in series to the transducer array 11.

The pulser 13 includes, for example, a plurality of pulse generators, adjusts a delay amount of each drive signal based on a transmission delay pattern selected according to a control signal from the main body control unit 27 such that ultrasound waves to be transmitted from the plurality of transducers of the transducer array 11 form ultrasound beams, and supplies the drive signal whose delay amount has been adjusted, to the plurality of transducers. Thus, in a case in which a pulsed or continuous-wave voltage is applied to the electrodes of the transducers of the transducer array 11, the piezoelectric body expands and contracts to generate a pulsed or continuous-wave ultrasound wave from each transducer, and an ultrasound beam is formed from a combined wave of these ultrasound waves.

The transmitted ultrasound beam is reflected by a target, for example, a site of the subject, and an ultrasound echo propagates toward the transducer array 11 of the ultrasound probe 1. The ultrasound echo propagating toward the transducer array 11 in this manner is received by each of the transducers constituting the transducer array 11. In this case, each transducer constituting the transducer array 11 expands and contracts by receiving the propagating ultrasound echo to generate a reception signal that is an electric signal, and outputs the reception signal to the amplification unit 14.

The amplification unit 14 amplifies the signal input from each of the transducers constituting the transducer array 11 and transmits the amplified signal to the AD conversion unit 15. The AD conversion unit 15 converts the signal transmitted from the amplification unit 14 into digital reception data, and transmits the reception data to the beam former 16. The beam former 16 performs so-called reception focus processing by giving and adding delay with respect to each reception data converted by the AD conversion unit 15, in accordance with a sound velocity or a sound velocity distribution set based on a reception delay pattern selected according to a control signal from the main body control unit 27. By this reception focus processing, each reception data converted by the AD conversion unit 15 is phase-added, and a sound ray signal in which the focus of the ultrasound echo is narrowed down is acquired.

Figure 3:
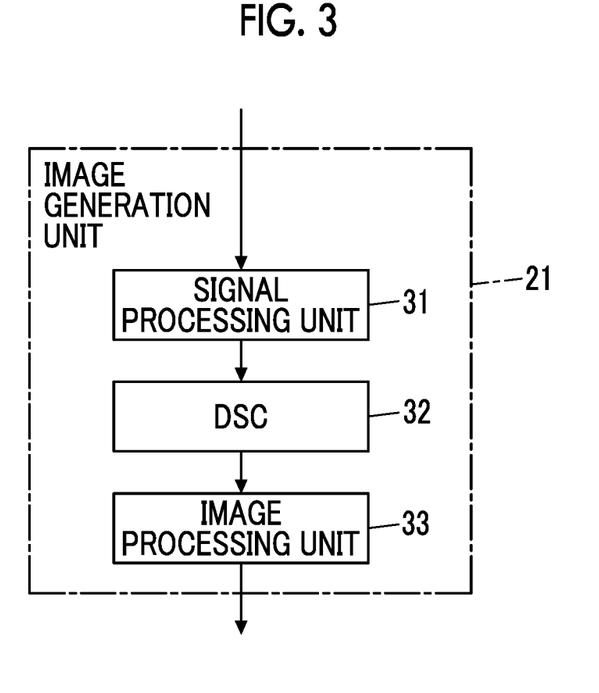
FIG. 3 is a block diagram showing an internal configuration of an image generation unit in the first embodiment.

The image generation unit 21 of the apparatus main body 2 cooperates with the ultrasound probe 1 to form the image acquisition unit 41 that acquires the ultrasound image, and has a configuration in which a signal processing unit 31, a digital scan converter (DSC) 32, and an image processing unit 33 are sequentially connected in series, as shown in FIG. 3.

The signal processing unit 31 performs, on the sound ray signal sent from the transmission and reception circuit 12 of the ultrasound probe 1, correction of attenuation due to a distance according to a depth of a reflection position of the ultrasound wave and then performs envelope detection processing, thereby generating an ultrasound image signal (B-mode image signal), which is tomographic image information related to tissues in the subject.

The DSC 32 converts (raster-converts) the ultrasound image signal generated by the signal processing unit 31 into an image signal according to a normal television signal scanning method.

The image processing unit 33 performs various kinds of necessary image processing such as gradation processing on the ultrasound image signal which is input from the DSC 32, and then outputs a signal representing the ultrasound image to the display control unit 22 and the image memory 24. The signal representing the ultrasound image generated by the image generation unit 21 in this manner is simply referred to as the ultrasound image.

The display control unit 22 performs predetermined processing on the ultrasound image sent from the image generation unit 21 under the control of the main body control unit 27, and displays the ultrasound image on the monitor 23.

The monitor 23 displays the ultrasound image under the control of the display control unit 22, and includes, for example, a display device such as a liquid crystal display (LCD) or an organic electroluminescence display (organic EL display).

The image memory 24 is a memory that stores the ultrasound image generated by the image generation unit 21 under the control of the main body control unit 27. For example, the image memory 24 can store a plurality of frames of ultrasound images generated by the image generation unit 21 in correspondence with diagnosis on a mammary cyst formed in a breast of the subject.

Here, the plurality of frames of ultrasound images include at least a first ultrasound image and a second ultrasound image obtained by imaging the cyst of the breast of the subject. The first ultrasound image is generated by the image generation unit 21, for example, by imaging the cyst of the breast in a state where the subject is in a first posture. On the other hand, the second ultrasound image is generated by the image generation unit 21, for example, by imaging the cyst from the same direction as that in a case of capturing the first ultrasound image with respect to the cyst in a state where the subject is in a second posture different from the first posture and an influence of the gravity (external force) different from that in a case of capturing the first ultrasound image acts on the cyst.

For example, after the first ultrasound image is captured with the posture of the subject in a supine posture, the second ultrasound image can be captured from the same direction as that in a case of capturing the first ultrasound image with respect to the cyst of the breast of the subject with the posture of the subject in either the left or right lateral decubitus posture. Accordingly, the first ultrasound image and the second ultrasound image can be acquired and stored in the image memory 24 in a state where the influences of the gravity acting on the cyst of the breast of the subject are different from each other.

The second ultrasound image is not limited to being captured in a state where the influence of the gravity different from that in a case of capturing the first ultrasound image is acting on the cyst, and may be captured after the influence of the gravity different from that in a case of capturing the first ultrasound image has acted on the cyst. For example, it is also possible to capture the first ultrasound image with the posture of the subject in a supine posture, change the posture of the subject to a lateral decubitus posture, and then return the posture of the subject to a supine posture to capture the second ultrasound image. In addition, the first ultrasound image and the second ultrasound image may be captured before and after shaking a body of the subject from side to side.

The external force acting on the cyst of the breast is not limited to the gravity, and for example, a contact pressure for pressing the ultrasound probe 1 against a body surface of the subject can also be used as the external force. That is, the first ultrasound image and the second ultrasound image may be acquired by changing only the contact pressure of the ultrasound probe 1 while the posture of the subject is kept constant and a position and an angle of the ultrasound probe 1 with respect to the breast of the subject are kept constant. By changing the contact pressure of the ultrasound probe 1, the first ultrasound image and the second ultrasound image are acquired in a state where different external forces act on the cyst of the breast. In this case as well, the contact pressure of the ultrasound probe 1 can be changed once, and then returned to the original contact pressure to acquire the second ultrasound image.

The first ultrasound image and the second ultrasound image thus acquired and stored in the image memory 24 are displayed on the monitor 23 via the display control unit 22.

As the image memory 24, a recording medium, such as a flash memory, a hard disc drive (HDD), a solid state drive (SSD), a flexible disc (FD), a magneto-optical disc (MO disc), a magnetic tape (MT), a random access memory (RAM), a compact disc (CD), a digital versatile disc (DVD), a secure digital card (SD card), or a universal serial bus memory (USB memory), can be used.

The debris specifying unit 25 specifies a cyst from each of the first ultrasound image and the second ultrasound image stored in the image memory 24, and further specifies debris in the specified cyst. Since the specification of the debris is performed for recognizing the movement of the debris in the cyst, as a premise thereof, it is necessary to confirm that the first ultrasound image and the second ultrasound image are images of the same cyst and are captured from the same direction with respect to the cyst.

Figure 4:
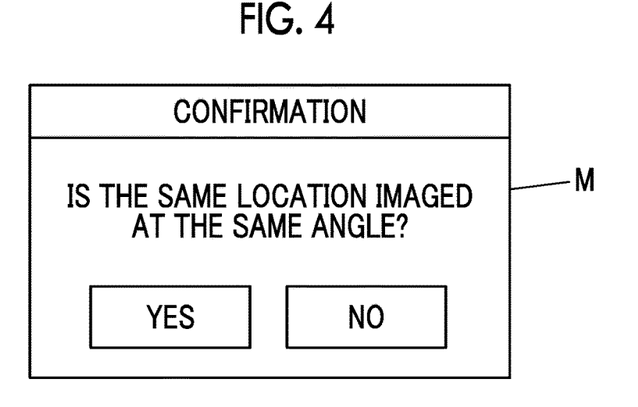
FIG. 4 is a diagram showing a confirmation message issued by a confirmation unit of a debris specifying unit according to the first embodiment.

Therefore, the debris specifying unit 25 has the confirmation unit 30 inside, and, after the second ultrasound image is captured following the first ultrasound image and stored in the image memory 24, the confirmation unit 30 causes the monitor 23 to display a confirmation message M, for example, as shown in FIG. 4 via the display control unit 22. Accordingly, while viewing the first ultrasound image and the second ultrasound image displayed on the monitor 23, a user is further prompted by the confirmation message M displayed on the monitor 23 and confirms whether or not the first ultrasound image and the second ultrasound image are images of the same location imaged at the same angle. In this case, the user can perform the confirmation based on a positional relationship between the cyst and a surrounding tissue structure captured in each of the first ultrasound image and the second ultrasound image.

In a case in which the user inputs "Yes" in response to the confirmation message M, it is determined that it has been confirmed that the same cyst has been imaged at the same angle, and the debris specifying unit 25 extracts a contour of the cyst being imaged from each of the first ultrasound image and the second ultrasound image by performing image recognition. The extracted contour of the cyst is highlighted on, for example, the first ultrasound image and the second ultrasound image displayed on the monitor 23. As the highlighting, various methods can be used, such as displaying a contour line of the cyst in a different color, displaying the contour line of the cyst with a thick line, and displaying an annotation indicating that there is the cyst in the vicinity of the contour line.

Figure 5:
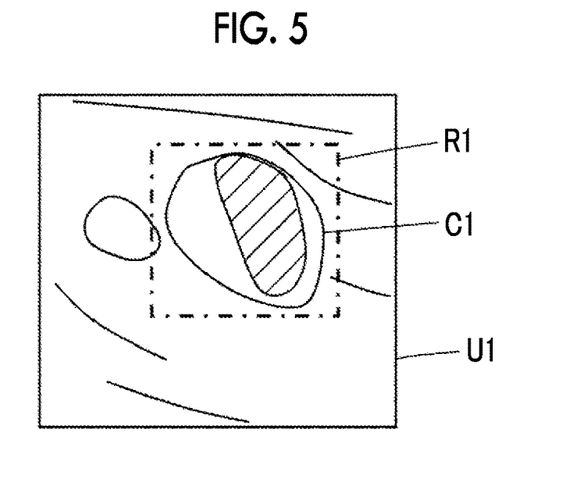
FIG. 5 is a diagram showing a search region designated for a first ultrasound image according to the first embodiment.

In this case, since a plurality of cysts may be present in an image, for example, as shown in FIG. 5, the user can designate a search region R1, which includes a cyst C1 to be diagnosed, in a first ultrasound image U1, and a contour of the cyst C1 can be extracted by performing image recognition on an inside of the search region R1.

Figure 6:
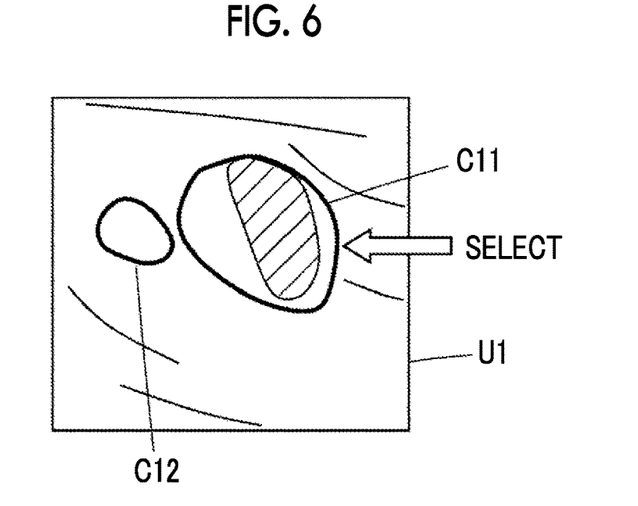
FIG. 6 is a diagram showing a plurality of cysts extracted from a first ultrasound image in a modification example.

Alternatively, as shown in FIG. 6, a configuration may be adopted in which, in a case in which a plurality of cysts C11 and C12 are extracted as a result of performing image recognition on the entire first ultrasound image U1, the user selects one cyst to be diagnosed from the plurality of cysts C11 and C12.

In addition, a configuration can be adopted in which, in a case in which the user views the contour line highlighted on the monitor 23 and determines that the contour of the cyst is not accurately represented, the user can manually modify the contour line.

Figure 7:
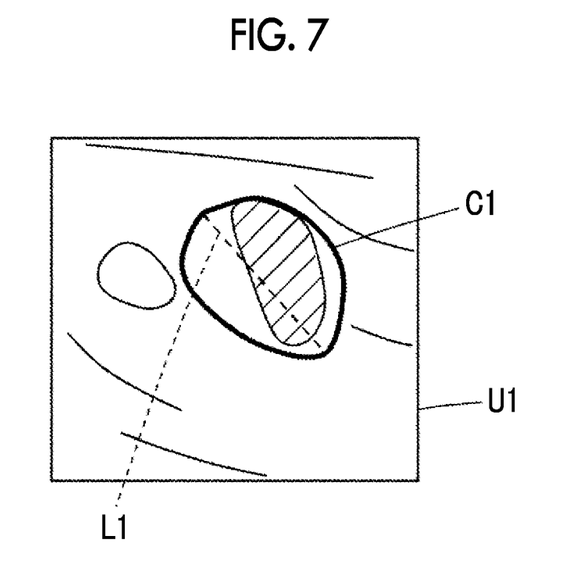
FIG. 7 is a diagram showing a cyst specified from the first ultrasound image according to the first embodiment.
Figure 8:
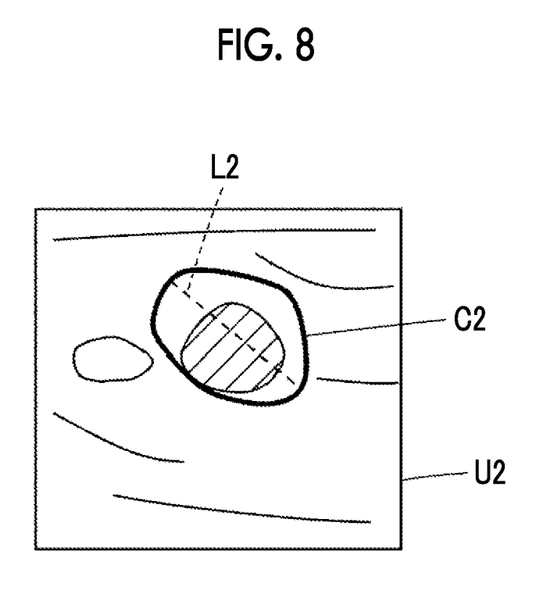
FIG. 8 is a diagram showing a cyst specified from a second ultrasound image in the first embodiment.

FIG. 7 and FIG. 8 show a cyst C1 of a first ultrasound image U1 and a cyst C2 of a second ultrasound image U2 in which the contour line is highlighted in this manner.

The first ultrasound image U1 and the second ultrasound image U2 are captured in a state where external forces different from each other act on the cyst of the breast of the subject by a change in the posture of the subject or the like. Therefore, even in a case in which the same cyst is imaged in the first ultrasound image U1 and the second ultrasound image U2, it is considered that the cyst in one ultrasound image is deformed with respect to the cyst in the other ultrasound image.

Figure 9:
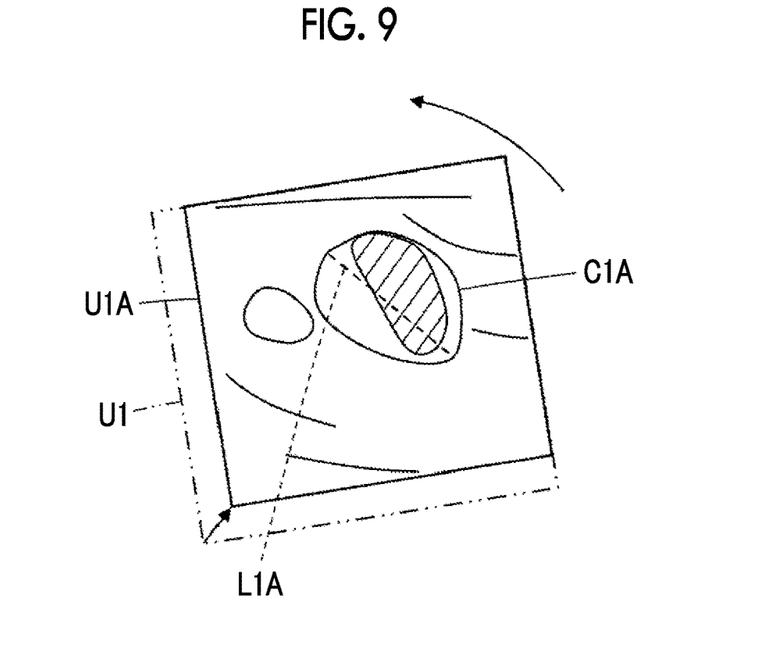
FIG. 9 is a diagram showing a cyst of the first ultrasound image registered with respect to a cyst of the second ultrasound image.

Therefore, the debris specifying unit 25 performs registration of the cyst between the first ultrasound image U1 and the second ultrasound image U2. Here, the registration is assumed to include reduction, enlargement, and rotation of the cyst. For example, a major axis L1 of the cyst C1 of the first ultrasound image U1 shown in FIG. 7 is longer than a major axis L2 of the cyst C2 of the second ultrasound image U2 shown in FIG. 8, and is located at a position rotated in a clockwise direction with respect to the major axis L2 of the cyst C2 by several degrees. Accordingly, for example, as shown in FIG. 9, the first ultrasound image U1 is reduced and rotated in a counterclockwise direction by several degrees to form a modified first ultrasound image U1A. Accordingly, a cyst C1A of the first ultrasound image U1A can be registered with respect to the cyst C2 of the second ultrasound image U2.

Instead of deforming the first ultrasound image U1 in accordance with the second ultrasound image U2, the second ultrasound image U2 may be deformed such that the cyst C2 of the second ultrasound image U2 is registered with respect to the cyst C1 of the first ultrasound image U1.

In addition, as a method of performing the registration between the cyst C1 of the first ultrasound image U1 and the cyst C2 of the second ultrasound image U2 by the debris specifying unit 25, for example, a known method such as a morphing technique as disclosed in JP2001-120529A can be used.

The debris specifying unit 25 specifies the debris by performing image recognition on an inside of the cyst C1A of the first ultrasound image U1A and an inside of the cyst C2 of the second ultrasound image U2 registered with each other in this manner.

The debris consists of an echogenic composition that reflects an ultrasound wave. Therefore, in a B-mode image, a portion of the cysts C1A and C2 in which the debris is present is depicted with relatively high brightness with respect to a portion in which the debris is not present. Therefore, the debris specifying unit 25 can specify the debris by extracting a region having brightness exceeding a predetermined threshold value inside the cysts C1A and C2.

In order to specify the cyst and specify the debris described above, image recognition can be performed using at least one of a determination model that has been trained by using a machine learning technique such as deep learning, template matching, or an image analysis technique using feature amounts such as adaptive boosting (Adaboost), support vector machine (SVM), or scale-invariant feature transform (SIFT).

The determination model is a trained model that has learned a cyst and a region (segmentation) in the cyst in a learning ultrasound image obtained by imaging a mammary gland.

The debris movement information providing unit 26 of the apparatus main body 2 provides information regarding the movement of the debris, which is specified by the debris specifying unit 25, in the cysts C1A and C2 between the first ultrasound image U1A and the second ultrasound image U2 registered with each other.

Figure 10:
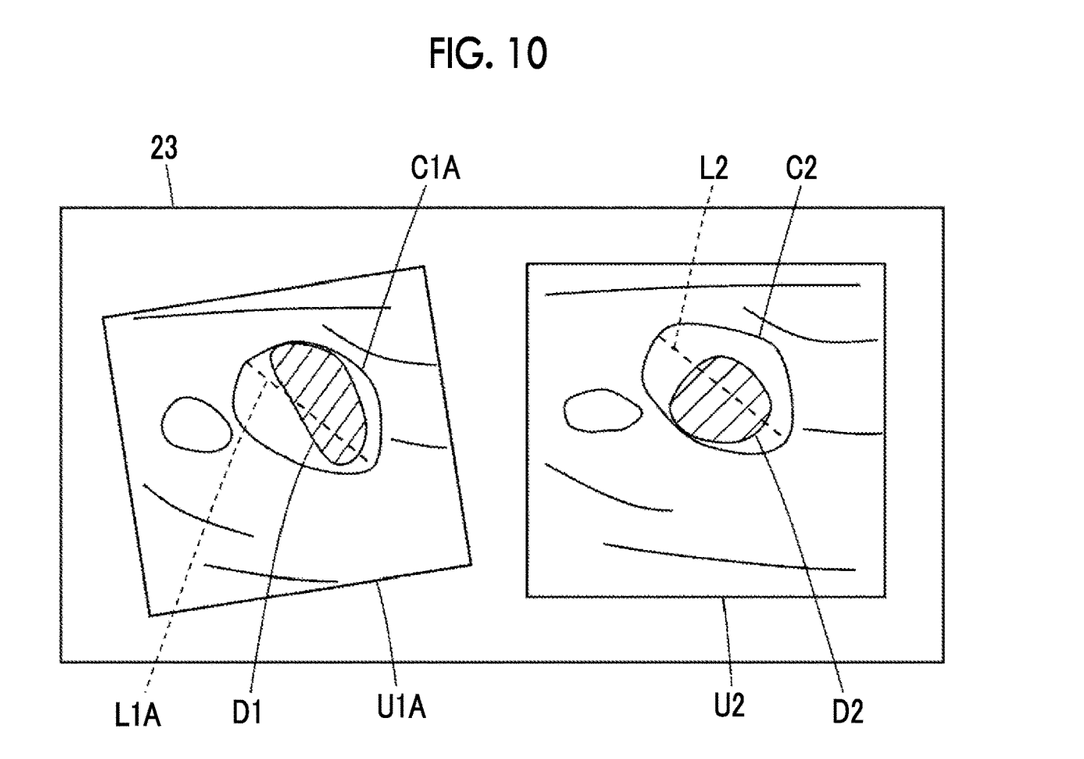
FIG. 10 is a diagram showing a state where the cyst of the first ultrasound image and the cyst of the second ultrasound image registered with each other are displayed side by side on a monitor.

Specifically, for example, as shown in FIG. 10, the debris movement information providing unit 26 displays the cyst C1A of the first ultrasound image U1A and the cyst C2 of the second ultrasound image U2, in which the debris is specified by the debris specifying unit 25, side by side on the monitor 23 via the display control unit 22.

The cyst C1A of the first ultrasound image U1A and the cyst C2 of the second ultrasound image U2 shown in FIG. 10 are registered with each other by the debris specifying unit 25, and a major axis L1A of the cyst C1A of the first ultrasound image U1A has the same length and the same angle as the major axis L2 of the cyst C2 of the second ultrasound image U2. Here, the term "same angle" means that inclinations of the major axes L1A and L2 with respect to an optional axis are the same. The optional axis may be, for example, an X axis extending in a horizontal direction. In addition, debris D1 and D2 specified by the debris specifying unit 25 are shown inside the cyst C1A of the first ultrasound image U1A and the cyst C2 of the second ultrasound image U2, respectively.

By displaying the cyst C1A of the first ultrasound image U1A and the cyst C2 of the second ultrasound image U2, which are registered with each other, side by side on the monitor 23, the user can easily recognize the movement from the debris D1 in the cyst C1A to the debris D2 in the cyst C2 by comparing the first ultrasound image U1A the second ultrasound image U2 on the monitor 23.

In FIG. 10, by comparing the first ultrasound image U1A and the second ultrasound image U2 displayed side by side on the monitor 23, it is easily confirmed that the debris D2 in the second ultrasound image U2 is moved in the cyst C2 with respect to the debris D1 in the first ultrasound image U1A. As a result, the user can recognize that the debris D1 and D2 to be diagnosed have fluidity for allowing the debris to move in the cysts C1A and C2 in response to the change in the posture of the subject, and that the cysts C1A and the C2 are so-called complicated cysts.

The debris movement information providing unit 26 can also highlight the debris D1 and D2 so that the movement of the debris D1 and D2 in the cysts C1A and C2 can be recognized more clearly. As the highlighting, various methods can be used, such as increasing brightness of a region where the debris D1 and D2 are present, displaying the region where the debris D1 and D2 are present in a different color from the periphery, and displaying the contour line of the debris D1 and D2 with a thick line or in a different color.

In addition, the debris D1 specified in the cyst C1A of the first ultrasound image U1A and the debris D2 specified in the cyst C2 of the second ultrasound image U2 may be displayed in a superimposed manner on the monitor 23 such that the debris movement information providing unit 26 can more clearly recognize the movement of the debris D1 and D2 in the cysts C1A and C2.

Figure 11:
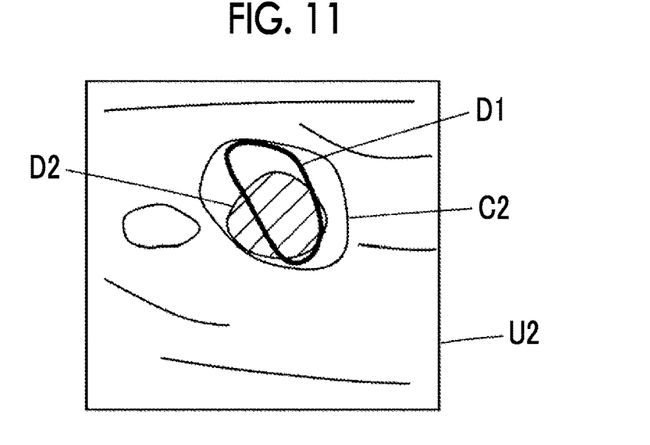
FIG. 11 is a diagram showing a state where a contour line of debris specified from the first ultrasound image is superimposed and displayed on debris specified from the second ultrasound image.

In this case, in order to make it easier to view the debris D1 and D2 displayed to be superimposed on each other, for example, as shown in FIG. 11, the contour line of the debris D1 extracted from the first ultrasound image U1A can be displayed to be superimposed on the debris D2 of the cyst C2 of the second ultrasound image U2. By observing the debris D1 and D2 displayed to be superimposed on each other, the user can easily confirm that the debris D2 fluidly moves with respect to the debris D1, and can recognize that the cysts C1A and C2 are so-called complicated cysts.

Figure 12:
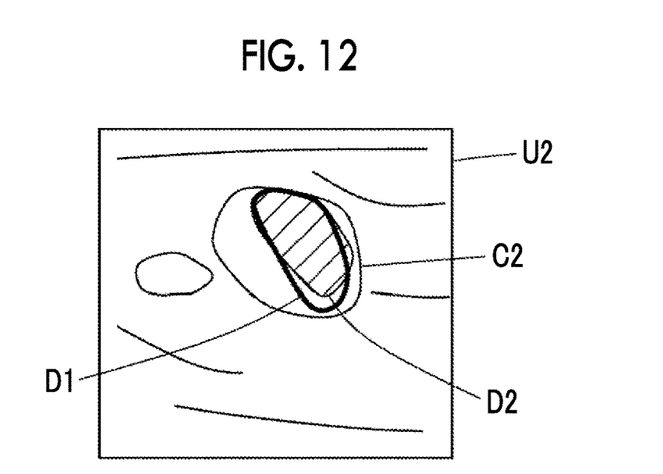
FIG. 12 is a diagram showing a state where the contour line of the debris specified from the first ultrasound image is superimposed and displayed on another debris specified from the second ultrasound image.

In a case in which, as shown in FIG. 12, the contour line of the debris D1 displayed to be superimposed on the debris D2 of the cyst C2 of the second ultrasound image U2 is not recognized to have substantially moved from the debris D2, the user can recognize that the debris D1 and D2 are solids having no fluidity for allowing the debris to move in the cysts C1A and C2 even in a case in which the posture of the subject is changed, and that there is a suspicion of a so-called complex cyst, in which a tumor is present in the cysts C1A and C2.

Figure 13:
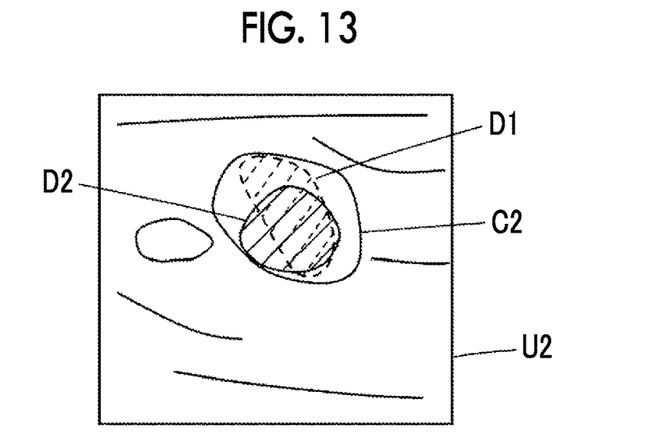
FIG. 13 is a diagram showing a state where the debris specified from the first ultrasound image is superimposed and displayed on the debris specified from the second ultrasound image.

In addition, instead of displaying the contour line of the debris D1 extracted from the first ultrasound image U1A, the debris movement information providing unit 26 may display each pixel inside the debris D1 to be superimposed on the debris D2 of the cyst C2 of the second ultrasound image U2 in a different color from the second ultrasound image U2 and with a predetermined transparency (alpha value), as shown in FIG. 13.

The main body control unit 27 of the apparatus main body 2 shown in FIG. 1 controls each unit of the apparatus main body 2 and the transmission and reception circuit 12 of the ultrasound probe 1, based on a control program or the like stored in advance.

In addition, although not shown, a main body-side storage unit is connected to the main body control unit 27. The main body-side storage unit stores a control program or the like. Examples of the main body-side storage unit include a flash memory, a random access memory (RAM), a secure digital card (SD card), and a solid state drive (SSD).

The input device 28 is a device for a user to perform an input operation, and includes, for example, a device such as a keyboard, a mouse, a track ball, a touch pad, and a touch sensor disposed on the monitor 23 in a superimposed manner.

The processor 29 including the image generation unit 21, the display control unit 22, the debris specifying unit 25, the debris movement information providing unit 26, and the main body control unit 27 is configured of a central processing unit (CPU) and a control program causing the CPU to perform various processes, but may be configured by using a field programmable gate array (FPGA), a digital signal processor (DSP), an application specific integrated circuit (ASIC), a graphics processing unit (GPU), or other integrated circuits (ICs), or may be configured by using a combination thereof.

In addition, the image generation unit 21, the display control unit 22, the debris specifying unit 25, the debris movement information providing unit 26, and the main body control unit 27 of the processor 29 can also be configured by being integrated partially or entirely into one CPU or the like.

Figure 14:
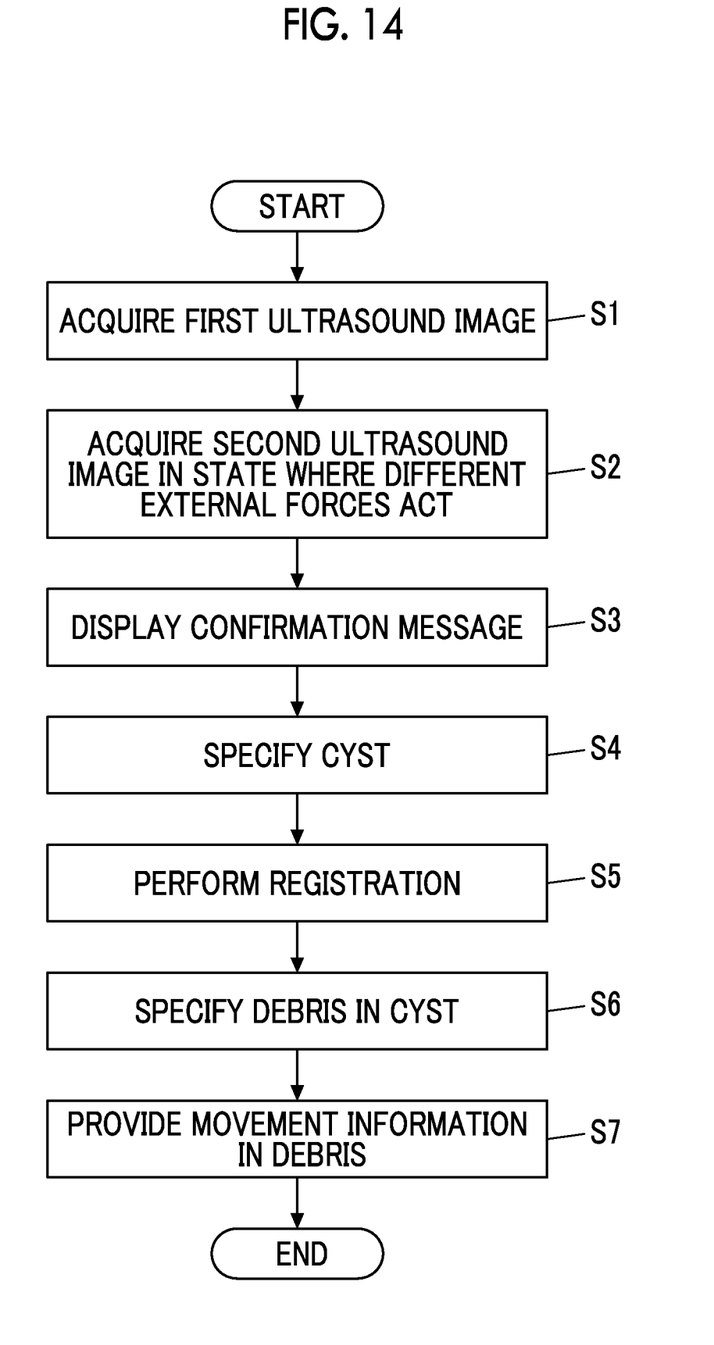
FIG. 14 is a flowchart showing an operation of the ultrasound diagnostic apparatus according to the first embodiment.

Next, an operation of the ultrasound diagnostic apparatus according to the first embodiment will be described with reference to a flowchart shown in FIG. 14.

First, in step S1, for example, in a state where the subject is in a supine posture as the first posture, the cyst of the breast of the subject is imaged by the image acquisition unit 41, and the first ultrasound image U1 is acquired. In this case, under the control of the main body control unit 27, transmission and reception of ultrasound waves from the plurality of transducers of the transducer array 11 are started according to the drive signal from the pulser 13 of the transmission and reception circuit 12. An ultrasound echo from an inside of a pharynx of the subject is received by the plurality of transducers of the transducer array 11. A reception signal, which is an analog signal, is output to the amplification unit 14, amplified, and then subjected to AD conversion by the AD conversion unit 15 to acquire reception data.

The reception focusing processing is performed on the reception data by the beam former 16. The sound ray signal generated thereby is sent to the image generation unit 21 of the apparatus main body 2, and the image generation unit 21 generates a first ultrasound image U1 representing tomographic image information regarding the cyst of the breast of the subject. In this case, the signal processing unit 31 of the image generation unit 21 performs the correction of attenuation according to the depth of the reflection position of the ultrasound wave and the envelope detection processing on the sound ray signal. In addition, the DSC 32 converts the obtained signal into an image signal according to a normal television signal scanning method. Further, the image processing unit 33 performs various kinds of necessary image processing such as gradation processing.

The first ultrasound image U1 generated by the image generation unit 21 is displayed on the monitor 23 via the display control unit 22, and is stored in the image memory 24.

Next, in step S2, the posture of the subject is changed, for example, in a state where the subject is in either the left or right lateral decubitus posture as the second posture, the cyst of the breast of the subject is imaged again by the image acquisition unit 41, and the second ultrasound image U2 is acquired. In this case, by changing the posture of the subject, the second ultrasound image U2 is acquired in a state where an external force (gravity) different from that in a case of capturing the first ultrasound image U1 acts on the cyst of the breast of the subject. In addition, the second ultrasound image U2 is acquired by imaging the cyst of the breast of the subject from the same direction as that in a case of capturing the first ultrasound image U1.

The posture of the subject in a case of capturing the first ultrasound image U1 and in a case of capturing the second ultrasound image U2 is not limited to the supine posture and the lateral decubitus posture, and two images of the first ultrasound image U1 and the second ultrasound image U2 need only be captured with different postures of the subject, such as a sitting posture and a decubitus posture.

In addition, the first ultrasound image U1 and the second ultrasound image U2 may be acquired by allowing the external forces different from each other to act on the cyst of the breast by changing only the contact pressure of the ultrasound probe 1 while the posture of the subject is kept constant and the position and the angle of the ultrasound probe 1 with respect to the breast of the subject are kept constant.

The second ultrasound image U2 is generated by the image generation unit 21 of the apparatus main body 2, displayed on the monitor 23 via the display control unit 22, and stored in the image memory 24, as with the first ultrasound image U1.

In a case in which the first ultrasound image U1 and the second ultrasound image U2 are thus stored in the image memory 24, in step S3, the confirmation unit 30 of the debris specifying unit 25 causes the monitor 23 to display the confirmation message M of "is the same location imaged at the same angle?" via the display control unit 22, for example, as shown in FIG. 4. This prompts the user to confirm whether or not the first ultrasound image U1 and the second ultrasound image U2 are images of the same location of the breast of the subject at the same angle.

As a result of the confirmation, in a case in which the user determines that the second ultrasound image U2 is not an image in which the same location is imaged as that of the first ultrasound image U1 or that the second ultrasound image U2 is an image in which the same location is imaged but the imaging angle is different, and inputs "No" in response to the confirmation message M, the acquisition of the second ultrasound image U2 in step S2 is performed again. It is also possible to start over from the acquisition of the first ultrasound image U1 in step S1.

In a case in which the user inputs "Yes" in response to the confirmation message M, in step S4, the debris specifying unit 25 specifies the cyst from each of the first ultrasound image U1 and the second ultrasound image U2 by performing image recognition. In this case, as shown in FIG. 5, the user can designate the search region R1 in the first ultrasound image U1 and the second ultrasound image U2, and can extract the contour of the cyst by performing image recognition on the inside of the search region R1. In addition, as shown in FIG. 6, a configuration may be adopted in which, in a case in which a plurality of cysts are extracted as a result of performing image recognition on the first ultrasound image U1 and the second ultrasound image U2, the user selects one cyst to be diagnosed from the plurality of cysts.

The cyst C1 of the first ultrasound image U1 and the cyst C2 of the second ultrasound image U2 specified by the debris specifying unit 25 are displayed on the monitor 23 with the highlighted contour lines, for example, as shown in FIGS. 7 and 8.

In step S5, further, the debris specifying unit 25 performs registration of the cysts C1 and C2 between the first ultrasound image U1 and the second ultrasound image U2. Accordingly, as shown in FIG. 9, the first ultrasound image U1A having the cyst C1A registered with the cyst C2 of the second ultrasound image U2 is formed. The major axis L1A of the cyst C1A of the first ultrasound image U1A has the same length and the same angle as the major axis L2 of the cyst C2 of the second ultrasound image U2.

Instead of forming the first ultrasound image U1A having the cyst C1A registered with the cyst C2 of the second ultrasound image U2, the second ultrasound image U2 may be deformed such that the cyst C2 of the second ultrasound image U2 is registered with respect to the cyst C1 of the first ultrasound image U1.

In subsequent step S6, the debris specifying unit 25 specifies the debris by performing image recognition on the inside of the cyst C1A of the first ultrasound image U1A and the inside of the cyst C2 of the second ultrasound image U2. That is, the debris specifying unit 25 specifies the debris D1 in the first ultrasound image U1A and the debris D2 in the second ultrasound image U2.

In this way, in a case in which the debris D1 and D2 of the first ultrasound image U1 and the second ultrasound image U2 are specified, in step S7, the debris movement information providing unit 26 displays the cyst C1A of the first ultrasound image U1A in which the debris D1 is specified and the cyst C2 of the second ultrasound image U2 in which the debris D2 is specified side by side on the monitor 23 via the display control unit 22, as debris movement information, as shown in FIG. 10.

Since the cyst C1A of the first ultrasound image U1A and the cyst C2 of the second ultrasound image U2 are already registered with each other in step S5, by displaying the first ultrasound image U1A and the second ultrasound image U2 side by side on the monitor 23, the user can easily and intuitively recognize the movement from the debris D1 in the cyst C1A to the debris D2 in the cyst C2 by comparing the first ultrasound image U1A the second ultrasound image U2 on the monitor 23.

Instead of displaying the cyst C1A of the first ultrasound image U1A and the cyst C2 of the second ultrasound image U2 side by side on the monitor 23, the debris movement information providing unit 26 can display the contour line of the debris D1 extracted from the first ultrasound image U1A to be superimposed on the debris D2 of the cyst C2 of the second ultrasound image U2, as shown in FIG. 11. In addition, as shown in FIG. 13, the debris movement information providing unit 26 may color each pixel inside the debris D1 and display the pixels to be superimposed on the debris D2 of the cyst C2 of the second ultrasound image U2 with a predetermined transparency.

In a case in which it is recognized that the debris D1 in the first ultrasound image U1A has moved in the cyst C1A and reached the debris D2 in the cyst C2 of the second ultrasound image U2, for example, as shown in FIGS. 10, 11, and 13, as a result of comparing the first ultrasound image U1A with the second ultrasound image U2, it can be recognized that the debris D1 and D2 have fluidity for allowing the debris to move in the cysts C1A and C2 in response to the change in the posture of the subject, and that the cysts C1A and C2 are so-called complicated cysts.

On the other hand, as shown in FIG. 12, in a case in which the debris D1 in the first ultrasound image U1A and the debris D2 in the second ultrasound image U2 are not recognized to have moved substantially with respect to each other, it can be recognized that the debris D1 and D2 are solids having no fluidity and that there is a suspicion of a so-called complex cyst, in which a tumor is present in the cysts C1A and C2.

As described above, according to the ultrasound diagnostic apparatus according to the first embodiment, the movement of the debris D1 and D2 in the cysts C1A and C2 can be easily recognized, and more accurate diagnosis can be performed.

Second Embodiment

Figure 15:
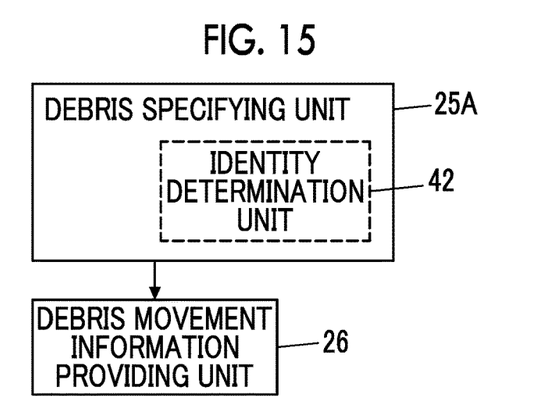
FIG. 15 is a block diagram showing an internal configuration of a debris specifying unit according to a second embodiment.

FIG. 15 shows an internal configuration of a debris specifying unit 25A in an ultrasound diagnostic apparatus according to a second embodiment. The debris specifying unit 25A has an identity determination unit 42, instead of the confirmation unit 30, in the debris specifying unit 25 used in the ultrasound diagnostic apparatus according to the first embodiment.

In the ultrasound diagnostic apparatus according to the first embodiment shown in FIG. 1, the debris specifying unit 25A can be used instead of the debris specifying unit 25.

The identity determination unit 42 automatically determines whether or not the same cyst is imaged by image recognition of each of the first ultrasound image U1 and the second ultrasound image U2.

Figure 16:
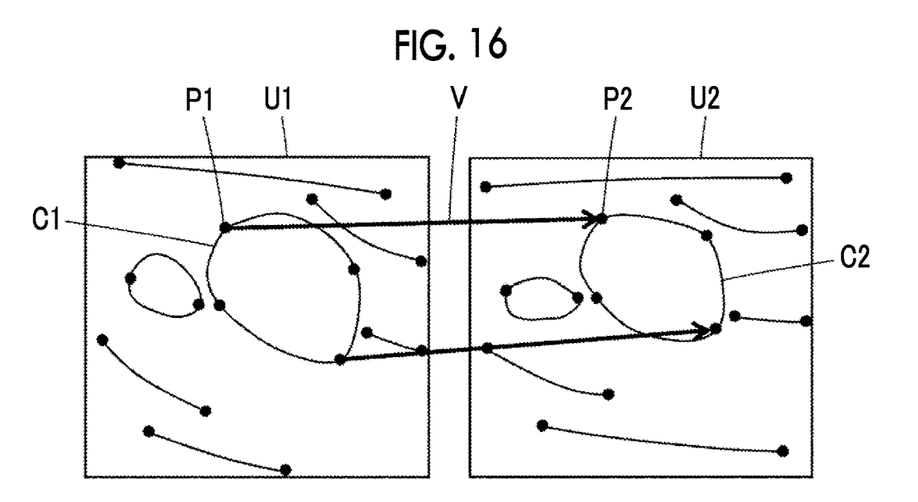
FIG. 16 is a diagram showing a movement vector calculated by an identity determination unit of the debris specifying unit according to the second embodiment.

Specifically, for example, as shown in FIG. 16, the identity determination unit 42 can detect an edge from each of the first ultrasound image U1 and the second ultrasound image U2, obtain a movement vector V in which a sample point P1 on the edge of the first ultrasound image U1 is moved to a sample point P2 on the edge of the second ultrasound image U2, and determine that the same cyst is imaged in a case in which the movement vector V falls within an allowable range.

Alternatively, the identity determination unit 42 can determine whether or not the same cyst is imaged by a trained determination model in which the first ultrasound image U1 and the second ultrasound image U2 are used as an input. The determination model is a model trained by using a machine learning technique such as deep learning. Specifically, in the determination model, a learning ultrasound image in which the cyst of the breast of the subject is imaged by changing the posture of the subject and the presence or absence of the cyst identity in the learning ultrasound image are used as training data. More specifically, the determination model is a trained model that has learned a plurality of training data regarding a relationship between the learning ultrasound image and the presence or absence of the cyst identity in the learning ultrasound image.

With the debris specifying unit 25A having such an identity determination unit 42, it is possible to determine whether or not the first ultrasound image U1 and the second ultrasound image U2 are images of the same cyst more accurately without displaying the confirmation message M as shown in FIG. 4 on the monitor 23.

Third Embodiment

Figure 17:
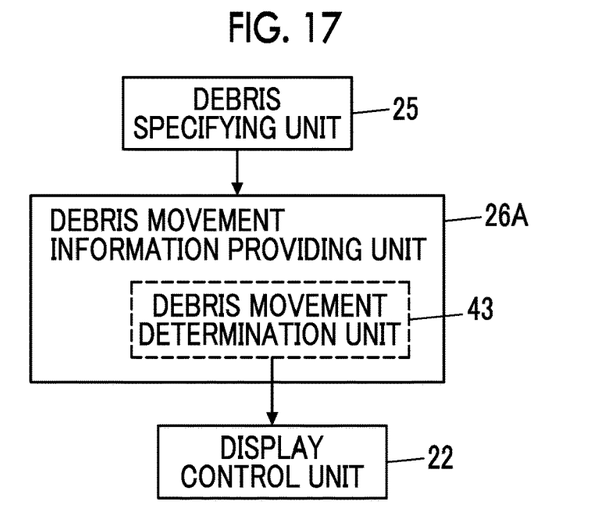
FIG. 17 is a block diagram showing an internal configuration of a debris movement information providing unit according to a third embodiment.

FIG. 17 shows an internal configuration of a debris movement information providing unit 26A in an ultrasonic diagnostic apparatus according to a third embodiment. The debris movement information providing unit 26A is obtained by providing a debris movement determination unit 43 in the debris movement information providing unit 26 used in the ultrasound diagnostic apparatus according to the first embodiment.

In the ultrasound diagnostic apparatus according to the first embodiment shown in FIG. 1, the debris movement information providing unit 26A can be used instead of the debris movement information providing unit 26.

The debris movement determination unit 43 calculates a movement amount from the debris D1 in the cyst C1A of the first ultrasound image U1A to the debris D2 in the cyst C2 of the second ultrasound image U2 by image recognition of the first ultrasound image U1A and the second ultrasound image U2 registered with each other by the debris specifying unit 25, and automatically determines whether or not the debris D1 and D2 substantially have moved in the cysts C1A and C2 based on the calculated movement amount of the debris D1 and D2.

As the movement amount of the debris D1 and D2, for example, a movement amount of centroid coordinates of the debris D1 and D2 can be used.

The debris movement determination unit 43 compares the calculated movement amount of the debris D1 and D2 with a predetermined threshold value, determines that substantial movement has occurred in a case in which the movement amount exceeds the threshold value, and displays, on the monitor 23, the fact that substantial movement has occurred, as a determination result. On the other hand, in a case in which the calculated movement amount of the debris D1 and D2 are equal to or less than the threshold value, it is determined that substantial movement has not occurred, and the fact that substantial movement has not occurred is displayed on the monitor 23, as a determination result.

The user can immediately recognize the state of movement of the debris D1 and D2 from the determination result displayed on the monitor 23.

The determination result by the debris movement determination unit 43 can be displayed on the monitor 23 in addition to the debris movement information consisting of the side-by-side display of the cyst C1A of the first ultrasound image U1A and the cyst C2 of the second ultrasound image U2 or the superimposed display of the debris D1 and D2 in the first embodiment. Alternatively, it is also possible to provide only the determination result by the debris movement determination unit 43 as the debris movement information by the debris movement information providing unit 26A and display it on the monitor 23.

In the first to third embodiments, the debris in the cyst (mammary cyst) formed in the breast of the subject has been described. However, the present invention is not limited to this, and can be similarly applied to debris in a cyst formed in a location other than the breast, such as debris in a cyst (thyroid cyst) formed in a thyroid gland.

The method of connecting the ultrasound probe 1 and the apparatus main body 2 in the first to third embodiments is not particularly limited, and a wired connection method or a wireless connection method may be used.

In the first to third embodiments, the ultrasound probe 1 includes the transmission and reception circuit 12. On the other hand, the apparatus main body 2 may include the transmission and reception circuit 12. In addition, the apparatus main body 2 includes the image generation unit 21. On the other hand, the ultrasound probe 1 may include the image generation unit 21. Further, the image generation unit 21 shown in FIG. 3 includes the signal processing unit 31, the DSC 32, and the image processing unit 33. On the other hand, the ultrasound probe 1 may include only the signal processing unit 31, and the apparatus main body 2 may include the DSC 32 and the image processing unit 33.

In addition, in the first to third embodiments, as the apparatus main body 2, a portable or handheld compact apparatus main body can be used, and a stationary apparatus main body can also be used.

EXPLANATION OF REFERENCES

1: ultrasound probe
2: apparatus main body
11: transducer array
12: transmission and reception circuit
13: pulser
14: amplification unit
15: AD conversion unit
16: beam former
21: image generation unit
22: display control unit
23: monitor
24: image memory
25A: debris specifying unit
26, 26A: debris movement information providing unit
27: main body control unit
28: input device
29: processor
30: confirmation unit
31: signal processing unit
32: DSC
33: image processing unit
41: image acquisition unit
42: identity determination unit
43: debris movement determination unit
U1: first ultrasound image
U2: second ultrasound image
C1, C1A, C11, C12, C2: cyst
R1: search region
L1, L1A, L2: major axis
D1, D2: debris
P1, P2: sample point
V: movement vector

What is claimed is:

1. An ultrasound diagnostic apparatus comprising:
a processor; and
a monitor,
wherein the processor acquires a first ultrasound image and a second ultrasound image obtained by imaging a cyst of a subject by transmitting and receiving an ultrasound wave to and from the subject, displays the first ultrasound image and the second ultrasound image on the monitor, specifies debris in the cyst from each of the first ultrasound image acquired, and the second ultrasound image acquired by imaging the cyst from the same direction as a direction in a case of capturing the first ultrasound image with respect to the cyst after an external force different from an external force in a case of capturing the first ultrasound image has acted on the cyst or in a state where the external force is acting on the cyst, and provides information regarding movement of the debris, which is specified, in the cyst between the first ultrasound image and the second ultrasound image.

2. The ultrasound diagnostic apparatus according to claim 1,
wherein the processor specifies the cyst from each of the first ultrasound image and the second ultrasound image, and specifies debris in the specified cyst.

3. The ultrasound diagnostic apparatus according to claim 2,
wherein the processor specifies the debris in a state where the cyst specified from the first ultrasound image and the cyst specified from the second ultrasound image are registered with each other.

4. The ultrasound diagnostic apparatus according to claim 3,
wherein the processor issues a message to a user to confirm that the cyst is imaged in the second ultrasound image from the same direction as the direction in a case of capturing the first ultrasound image.

5. The ultrasound diagnostic apparatus according to claim 3,
wherein the processor determines whether or not the same cyst is imaged by image recognition of each of the first ultrasound image and the second ultrasound image.

6. The ultrasound diagnostic apparatus according to claim 5,
wherein the processor detects an edge from each of the first ultrasound image and the second ultrasound image, obtains a movement vector in which the edge is moved between the first ultrasound image and the second ultrasound image, and determines that the same cyst is imaged in a case in which the movement vector falls within an allowable range.

7. The ultrasound diagnostic apparatus according to claim 5,
wherein the processor determines whether or not the same cyst is imaged by a trained determination model in which the first ultrasound image and the second ultrasound image are used as an input.

8. The ultrasound diagnostic apparatus according to claim 3,
wherein the processor displays, on the monitor, the cyst in the first ultrasound image and the cyst in the second ultrasound image registered with each other.

9. The ultrasound diagnostic apparatus according to claim 4,
wherein the processor displays, on the monitor, the cyst in the first ultrasound image and the cyst in the second ultrasound image registered with each other.

10. The ultrasound diagnostic apparatus according to claim 5,
wherein the processor displays, on the monitor, the cyst in the first ultrasound image and the cyst in the second ultrasound image registered with each other.

11. The ultrasound diagnostic apparatus according to claim 6,
wherein the processor displays, on the monitor, the cyst in the first ultrasound image and the cyst in the second ultrasound image registered with each other.

12. The ultrasound diagnostic apparatus according to claim 7,
wherein the processor displays, on the monitor, the cyst in the first ultrasound image and the cyst in the second ultrasound image registered with each other.

13. The ultrasound diagnostic apparatus according to claim 8,
wherein the processor displays the cyst in the first ultrasound image and the cyst in the second ultrasound image side by side on the monitor.

14. The ultrasound diagnostic apparatus according to claim 9,
wherein the processor displays the cyst in the first ultrasound image and the cyst in the second ultrasound image side by side on the monitor.

15. The ultrasound diagnostic apparatus according to claim 10,
wherein the processor displays the cyst in the first ultrasound image and the cyst in the second ultrasound image side by side on the monitor.

16. The ultrasound diagnostic apparatus according to claim 8,
wherein the processor displays the cyst in the first ultrasound image and the cyst in the second ultrasound image in a superimposed manner on the monitor.

17. The ultrasound diagnostic apparatus according to claim 9,
wherein the processor displays the cyst in the first ultrasound image and the cyst in the second ultrasound image in a superimposed manner on the monitor.

18. The ultrasound diagnostic apparatus according to claim 10,
wherein the processor displays the cyst in the first ultrasound image and the cyst in the second ultrasound image in a superimposed manner on the monitor.

19. The ultrasound diagnostic apparatus according to claim 3,
wherein the processor determines whether or not a movement amount of the debris in the cyst between the first ultrasound image and the second ultrasound image exceeds a threshold value by image recognition of each of the first ultrasound image and the second ultrasound image, and displays a determination result on the monitor.

20. A control method of an ultrasound diagnostic apparatus, the method comprising:
acquiring a first ultrasound image obtained by imaging a cyst of a subject;
displaying the first ultrasound image on a monitor;
acquiring a second ultrasound image obtained by imaging the cyst from the same direction as a direction in a case of capturing the first ultrasound image with respect to the cyst after an external force different from an external force in a case of capturing the first ultrasound image has acted on the cyst or in a state where the external force is acting on the cyst;
specifying debris in the cyst from each of the first ultrasound image and the second ultrasound image; and
providing information regarding movement of the debris in the cyst between the first ultrasound image and the second ultrasound image.

* * * * *